(12) United States Patent
Goh et al.

(10) Patent No.: US 12,415,665 B2
(45) Date of Patent: Sep. 16, 2025

(54) CONTAINER CAP FOR STORING SPECIMEN

(71) Applicant: BIONLIFESCIENCE, INC., Namyangju-si (KR)

(72) Inventors: Chang Wook Goh, Namyangju-si (KR); Joong Hwan Jeong, Bucheon-si (KR); Bong Yoon Kim, Goyang-si (KR)

(73) Assignee: BIONLIFESCIENCE, INC., Namyangju-si (KR)

( * ) Notice: Subject to any disclaimer, the term of this patent is extended or adjusted under 35 U.S.C. 154(b) by 48 days.

(21) Appl. No.: 18/567,012

(22) PCT Filed: May 4, 2022

(86) PCT No.: PCT/KR2022/006388
§ 371 (c)(1),
(2) Date: Dec. 4, 2023

(87) PCT Pub. No.: WO2022/255657
PCT Pub. Date: Dec. 8, 2022

(65) Prior Publication Data
US 2024/0270457 A1    Aug. 15, 2024

(30) Foreign Application Priority Data

Jun. 5, 2021 (KR) .................. 10-2021-0073139
May 3, 2022 (KR) .................. 10-2022-0054550

(51) Int. Cl.
*B65D 51/26* (2006.01)
*A61B 10/00* (2006.01)
(Continued)

(52) U.S. Cl.
CPC .......... *B65D 51/26* (2013.01); *A61B 10/0096* (2013.01); *A61B 10/02* (2013.01); *B65D 41/04* (2013.01)

(58) Field of Classification Search
CPC ............ A61B 10/0096; A61B 10/0045; A61B 10/0051; B01L 2300/042; B01L 3/5029
(Continued)

(56) References Cited

U.S. PATENT DOCUMENTS 2,835,246 A * 5/1958 Boettger .................. A61F 13/38
600/572
4,409,988 A * 10/1983 Greenspan ............ B01L 3/5029
435/304.2
(Continued)

FOREIGN PATENT DOCUMENTS

JP           5584287 B1    9/2014
KR      20110006453 U     6/2011
(Continued)

*Primary Examiner* — Anthony D Stashick
*Assistant Examiner* — Prince Pal
(74) *Attorney, Agent, or Firm* — NKL LAW; Jae Youn Kim

(57) ABSTRACT

The present invention can provide a container cap for storing a specimen, the container cap being characterized by comprising: a cap body which includes a tubular side portion and a bottom portion coupled to one end of the side portion, and is detachably screw-fastened to an open side of a specimen storage container in which one or more specimen collection swabs are inserted; an insertion coupling part which protrudes from the bottom portion toward the specimen storage container and has an inner space formed therein, wherein respective stick portions of the one or more specimen collection swabs are inserted into the inner space and fitted and coupled thereto; and a protrusion fitting part which is
(Continued)

positioned at the central portion of the inner space and protrudes from the bottom surface of the cover body.

6 Claims, 12 Drawing Sheets

(51) Int. Cl.
*A61B 10/02* (2006.01)
*B65D 41/04* (2006.01)

(58) Field of Classification Search
USPC ............... 422/411, 405, 406, 549, 547, 568
See application file for complete search history.

(56) References Cited

U.S. PATENT DOCUMENTS

| | | | | | |
|---|---|---|---|---|---|
| 4,803,998 | A | * | 2/1989 | Kezes | A61F 13/38 600/572 |
| 5,458,113 | A | * | 10/1995 | Burns | A61B 5/150343 422/547 |
| 5,543,115 | A | * | 8/1996 | Karakawa | A61B 10/0038 436/66 |
| 5,830,154 | A | * | 11/1998 | Goldstein | B01L 3/5029 600/572 |
| 5,965,453 | A | * | 10/1999 | Skiffington | C12Q 1/66 435/287.7 |
| 6,780,160 | B2 | * | 8/2004 | Zhou | A61B 10/0096 600/562 |
| 7,323,144 | B2 | * | 1/2008 | Arai | B01L 3/5021 422/534 |
| 7,517,497 | B2 | * | 4/2009 | Price | B26F 1/16 422/547 |
| 7,993,871 | B2 | * | 8/2011 | Skiffington | G01N 1/02 435/287.4 |
| 8,075,850 | B2 | * | 12/2011 | Sangha | B01L 99/00 422/406 |
| 8,623,665 | B2 | * | 1/2014 | Poll | A61B 10/0096 436/177 |
| 8,728,414 | B2 | * | 5/2014 | Beach | A61B 10/02 422/549 |
| 8,961,896 | B2 | * | 2/2015 | McSherry | C12M 1/30 600/572 |
| 9,027,420 | B1 | * | 5/2015 | Ward | G01N 1/02 73/864.71 |
| 10,004,444 | B2 | * | 6/2018 | Bauer | A61B 5/150343 |
| 11,325,129 | B2 | * | 5/2022 | Staton | B65D 1/36 |
| 11,709,175 | B2 | * | 7/2023 | Hopper | B01L 3/502 435/6.12 |
| D1,042,873 | S | * | 9/2024 | Goh | D24/119 |
| D1,042,879 | S | * | 9/2024 | Goh | D24/224 |
| 2004/0019295 | A1 | * | 1/2004 | Zhou | A61B 10/0096 600/562 |
| 2004/0019298 | A1 | * | 1/2004 | Zhou | A61B 10/0096 600/564 |
| 2005/0252820 | A1 | * | 11/2005 | Sanchez-Felix | A61B 10/0045 206/569 |
| 2006/0057027 | A1 | * | 3/2006 | Hudak | A61B 10/0051 422/549 |
| 2006/0115385 | A1 | * | 6/2006 | Jon Meyer | A61B 10/0096 422/547 |
| 2008/0206740 | A1 | * | 8/2008 | Skiffington | B01L 3/5029 435/5 |
| 2009/0156962 | A1 | * | 6/2009 | Yong | A61B 10/0045 600/569 |
| 2010/0043574 | A1 | * | 2/2010 | Katsumata | B01L 3/50825 422/400 |
| 2012/0009588 | A1 | * | 1/2012 | Rajagopal | C12Q 1/04 435/7.1 |
| 2012/0094303 | A1 | * | 4/2012 | Engel | G01N 33/54388 435/7.1 |
| 2012/0141341 | A1 | * | 6/2012 | Bartfeld | B01L 3/50825 422/549 |
| 2012/0220042 | A1 | * | 8/2012 | Sangha | G01N 1/02 422/411 |
| 2012/0220043 | A1 | * | 8/2012 | Sangha | G01N 1/02 422/411 |
| 2013/0216453 | A1 | * | 8/2013 | Eldridge | A61J 1/1412 422/550 |
| 2013/0302219 | A1 | * | 11/2013 | Li | B01L 3/50825 422/550 |
| 2014/0017147 | A1 | * | 1/2014 | Kim | B01L 3/50825 422/501 |
| 2017/0036205 | A1 | * | 2/2017 | Bishop | A61B 10/0045 |
| 2017/0071582 | A1 | * | 3/2017 | Buck | A61B 10/0051 |
| 2017/0260563 | A1 | * | 9/2017 | Lappalainen | G01N 33/528 |
| 2020/0056965 | A1 | * | 2/2020 | Gao | G01N 1/02 |
| 2020/0155125 | A1 | * | 5/2020 | Ouyang | C12M 1/30 |
| 2022/0338848 | A1 | * | 10/2022 | Martello | B01L 3/5029 |
| 2023/0172591 | A1 | * | 6/2023 | Robbins | B01L 3/5029 600/573 |
| 2023/0311130 | A1 | * | 10/2023 | Reber | B01L 7/52 422/600 |
| 2023/0355219 | A1 | * | 11/2023 | Ling | A61B 10/0045 |
| 2023/0363744 | A1 | * | 11/2023 | Goh | A61B 10/0051 |
| 2023/0397856 | A1 | * | 12/2023 | Walker | A61B 5/150022 |
| 2024/0042449 | A1 | * | 2/2024 | Hassberg | B01L 3/523 |
| 2024/0044750 | A1 | * | 2/2024 | Goh | A61B 10/02 |
| 2024/0188942 | A1 | * | 6/2024 | Johnson | A61B 10/0051 |
| 2024/0261788 | A1 | * | 8/2024 | Goh | A61B 10/0096 |
| 2024/0270457 | A1 | * | 8/2024 | Goh | B01L 3/50825 |
| 2024/0280449 | A1 | * | 8/2024 | Goh | B01L 3/50825 |
| 2025/0033036 | A1 | * | 1/2025 | Lei | B01L 3/5023 |

FOREIGN PATENT DOCUMENTS

| | | |
|---|---|---|
| KR | 101140751 B1 | 5/2012 |
| KR | 101284703 B1 | 7/2013 |
| KR | 101309066 B1 | 9/2013 |
| KR | 20200000438 U | 2/2020 |

* cited by examiner

CONTAINER CAP FOR STORING SPECIMEN

TECHNICAL FIELD

The present invention relates to a container cover for specimen storage, and more particularly to a container cover for specimen storage capable of more efficiently storing and transporting a specimen collected from a subject in order to identify or test for infection with various kinds of communicable diseases.

BACKGROUND ART

Due to the recent spread of COVID 19 (Corona Virus Disease 19), testing for infection has been actively conducted, and testing is done by collecting a specimen from a subject.

In contrast, for common respiratory diseases, a swab for specimen collection is inserted into the nasal cavity or oral cavity of a subject, secretions are collected from the mucous membrane of the nasal cavity or oral cavity lining, and the secretions are examined to test for respiratory diseases.

Although recently prevalent COVID 19 is a respiratory disease, secretions are collected from both the mucous membranes of the nasal cavity and the oral cavity lining of the subject in order to improve accuracy of the test. After specimens are collected, collection sticks are placed in a specimen preservation container containing a preservation solution (medium), and the specimen preservation container is stored or transported to a testing site.

Meanwhile, a conventional specimen collection and storage kit configured to collect and store a specimen includes a swab configured to collect a specimen, a specimen container configured to receive a medium and to allow the swab having the collected specimen to be inserted thereinto so as to be stored therein, and a container cover for specimen storage configured to seal the specimen container.

However, the conventional specimen collection and storage kit is configured to allow only one swab to be inserted thereinto and stored therein. When specimens are collected from two or more body parts depending on the type of test, therefore, swabs having the collected specimens must be separately stored in different specimen collection and storage kits even though the specimens are from the same subject.

Because of this, it is difficult to store and manage the conventional specimen collection and storage kits due to requirement of more specimen collection and storage kits as well as the laborious task of repeatedly filling in information of the same subject on the respective specimen containers.

In addition, the conventional specimen collection and storage kits require an inspector to manually remove the swab having the collected specimen from the specimen container after transportation thereof to the testing site, which is not only cumbersome, but may also lead to unnecessary contamination during the swab removal process.

DISCLOSURE

Technical Problem

It is an object of the present invention to provide a container cover for specimen storage that allows a plurality of specimen collection swabs to be stored in a single specimen collection container when specimens are collected from two or more body parts of a subject, thereby improving workability and facilitating storage and management.

It is another object of the present invention to provide a container cover for specimen storage configured such that it is unnecessary for an inspector to perform a separate operation to remove a specimen collection swab from a specimen container, whereby it is possible to eliminate conventional inconvenience of removing the specimen collection swab and to prevent unnecessary contamination that may occur during the operation to remove the swab.

Technical Solution

The present invention provides a container cover for specimen storage, the container cover including a cover body comprising a tubular side portion and a bottom portion coupled to one end of the side portion, the cover body being detachably screwed to open one side of a specimen preservation container in which one or more specimen collection swabs are provided by insertion, an insertion coupling portion formed so as to protrude from the bottom portion toward the specimen preservation container, the insertion coupling portion having an inner space defined therein such that stick portions of the specimen collection swabs can inserted and fitted into and coupled to the inner space, and a protruding fitting portion located in the center of the inner space, the protruding fitting portion being formed so as to protrude from the bottom portion of the cover body, the protruding fitting portion being configured such that the stick portions are fitted and coupled between an outer surface of the protruding fitting portion and an inner surface of the insertion coupling portion, wherein, when the specimen preservation container is coupled to the container cover, the stick portions are fitted into and coupled to an arbitrary position in the inner space.

Advantageous Effects

In a container cover for specimen storage according to the present invention, it is possible to store a plurality of swabs having specimens collected from two or more body parts of a subject in a single specimen collection kit, whereby it is possible to dramatically reduce tasks, such as filling in information of the subject, and therefore it is possible to improve workability, and it is possible to reduce the number of specimen collection and storage kits, and therefore it is possible to reduce a space necessary for storage and to achieve easier storage and management.

In addition, the container cover for specimen storage according to the present invention is configured such that, when the container cover for specimen storage is removed, specimen collection swabs are also removed from a specimen preservation container without the need for an inspector to remove the specimen collection swabs from the specimen preservation container using tweezers, whereby it is possible to prevent unnecessary contamination, and the need to remove the specimen collection swabs and to disinfect tools such as the tweezers is eliminated, whereby it is possible to eliminate operational inconvenience and to improve workability.

Also, in the container cover for specimen storage according to the present invention, it is possible to secure the force of fastening to the specimen preservation container and to improve airtightness and sealing force through an airtight portion, whereby it is possible to effectively prevent leakage of a specimen medium and contamination from the outside.

The container cover for specimen storage according to the present invention is simple in structure and has a reduced number of parts, whereby it is possible to reduce manufacturing costs, which is economical.

BEST MODE

Figure 1:
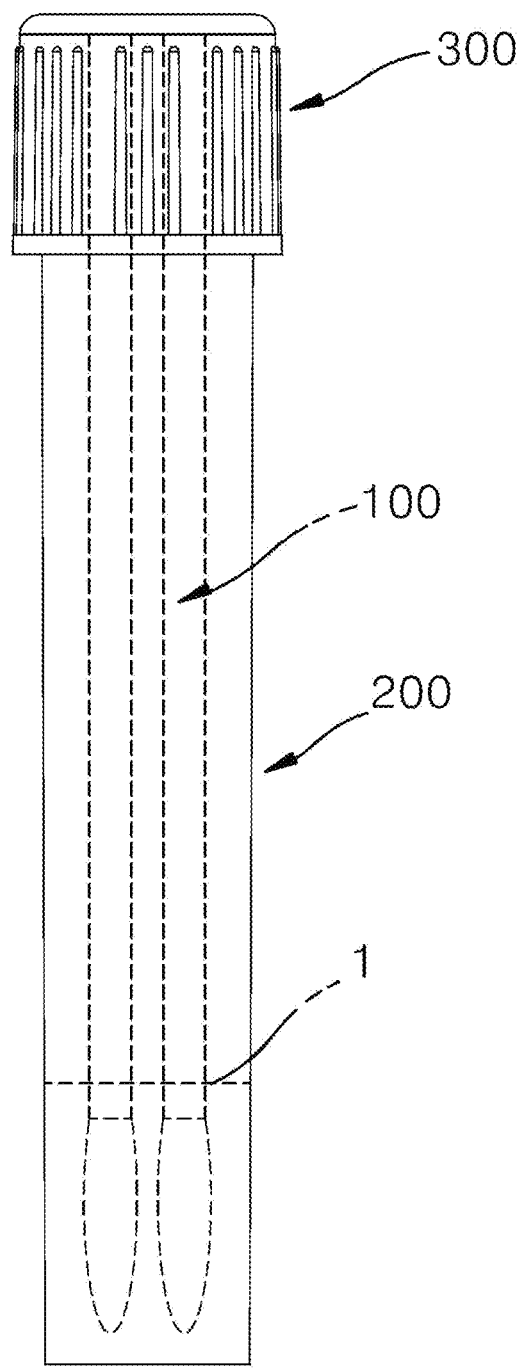
FIG. 1 is an exterior view showing the state in which a container cover for specimen storage according to an embodiment of the present invention is coupled to a container.

The present invention may be changed in various manners and may have various embodiments, wherein specific embodiments will be described with reference to the drawings. However, the present invention is not limited to the specific embodiments, and it should be understood that the present invention includes all modifications, equivalents, or substitutions included in the idea and technical scope of the present invention.

Although terms including ordinal numbers, such as "first" and "second," may be used herein to describe various components, these components should not be limited by these terms. These terms are only used to distinguish one component from another component. For example, within the scope defined by the present invention, a first element may be referred to as a second element, and similarly, a second element may be referred to as a first element. The term "and/or" includes any and all combinations of one or more of the associated listed items.

It should be understood that, when a component is referred to as being "connected to" or "coupled to" another component, it may be directly connected to or coupled to another component or intervening components may be present. In contrast, it should be understood that, when a component is referred to as being "directly connected to" or "directly coupled to" another component, there are no intervening components present.

The terms used in the present application are provided only to described specific embodiments, and do not limit the present invention. Singular forms are intended to include plural forms as well, unless the context clearly indicates otherwise. In the present application, it should be understood that the terms "includes," "has," etc. specify the presence of stated features, numbers, steps, operations, elements, components, or combinations thereof, but do not preclude the presence or addition of one or more other features, numbers, steps, operations, elements, components, or combinations thereof.

Unless otherwise defined, all terms, including technical and scientific terms, used in this specification have the same meanings as those commonly understood by a person having ordinary skill in the art to which the present invention pertains. It will be further understood that terms, such as those defined in commonly used dictionaries, should be interpreted as having meanings consistent with their meanings in the context of the relevant art and the present disclosure, and are not to be interpreted in an idealized or overly formal sense unless expressly so defined herein. Also, in describing the present invention, identical reference numerals are used for identical components in the drawings, and duplicate descriptions of identical components will be omitted for ease of overall understanding.

A specimen collection and storage kit according to an embodiment of the present invention is configured such that, when specimens are collected from two or more body parts of a subject, specimen collection swabs 100 can be stored in a single specimen preservation container 200, such that it is possible to prevent contamination from the outside during storage and transportation due to good airtightness, and such that the specimen collection swabs 100 are removed from the specimen preservation container 200 together with a container cover 300 for specimen storage at the time of inspection without the need to remove the specimen collection swabs 100 from the specimen preservation container 200.

Hereinafter, preferred embodiments of the present invention will be described in more detail with reference to the accompanying drawings.

A container cover 300 for specimen storage according to an embodiment of the present invention is configured to be included in a specimen collection and storage kit, and the specimen collection and storage kit will first be described before describing the container cover 300 for specimen storage according to the present invention.

Figure 2:
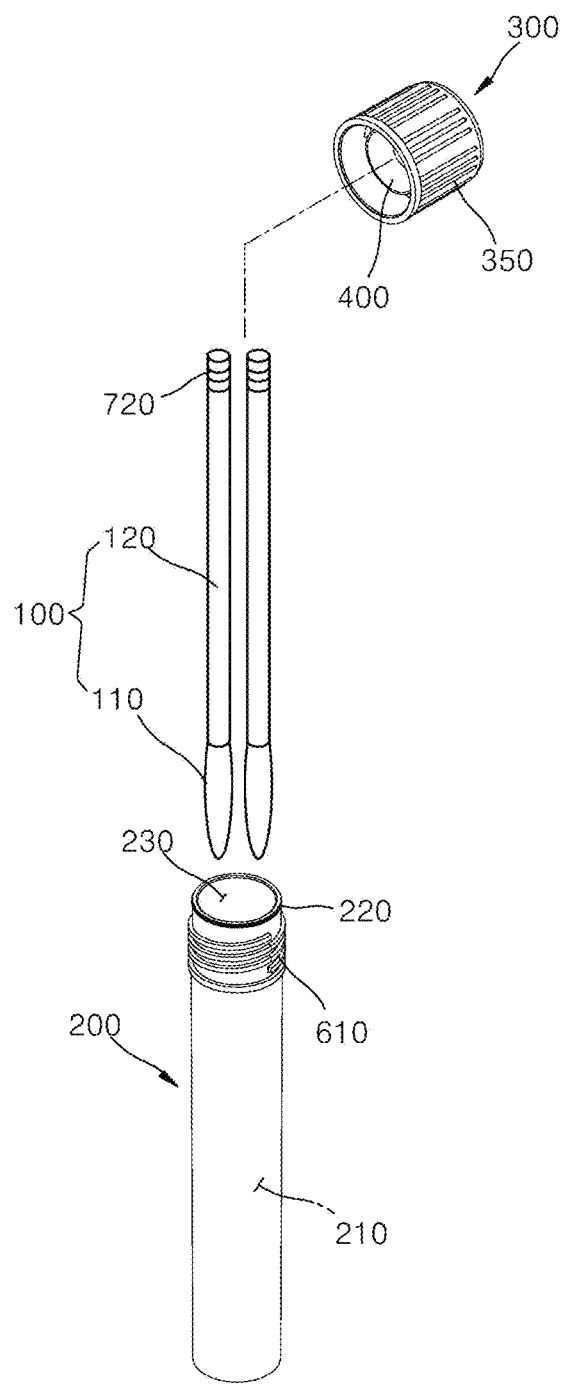
FIG. 2 is an exploded perspective view showing the container cover for specimen storage according to the embodiment of the present invention and the container.

FIGS. 1 and 2 are views showing a specimen collection and storage kit, wherein the specimen collection and storage kit includes a specimen collection swab 100, a specimen preservation container 200, and a container cover 300 for specimen storage according to the present invention.

First, the specimen collection swab 100, which is configured to collect a specimen from a subject, may be formed in the shape of a swab, as shown.

The specimen collection swab 100 may include a head portion 110 configured to collect a specimen and a stick portion 120 coupled to the head portion 110.

The head portion 110 may have a roughly spherically rounded shape, and may be made of a material, such as a fiber. That is, the head portion may be configured to have a shape and material that facilitate collection of a specimen from a subject.

The stick portion 120 may be formed in the shape of a stick, and may be configured such that one end of the stick portion is coupled to the head portion 110 and the other end of the stick portion can be gripped by an inspector.

The stick portion 120 may be formed to have a predetermined long length to facilitate insertion into the nasal cavity or oral cavity in order to easily collect a specimen.

The stick portion 120 may be provided with an incision (not shown) configured such that a part of incision can be cut by the inspector. When a specimen is collected, therefore, the stick portion 120 may be maintained long to facilitate specimen collection, and when the stick portion is inserted into the specimen preservation container 200 after specimen collection, the stick portion is cut so as to correspond to the length of the specimen preservation container 200, whereby it is possible to easily achieve shielding of the container cover 300 for specimen storage.

The specimen preservation container 200 may be formed in the shape of a cup shielded at one side, a receiving space 210 may be formed in the specimen preservation container such that a medium 1 and the specimen collection swab 100 are received and stored in the receiving space 210, and the specimen preservation container may be provided at the other open side thereof with an insertion hole 230, through which the specimen collection swab 100 is inserted.

Figure 3:
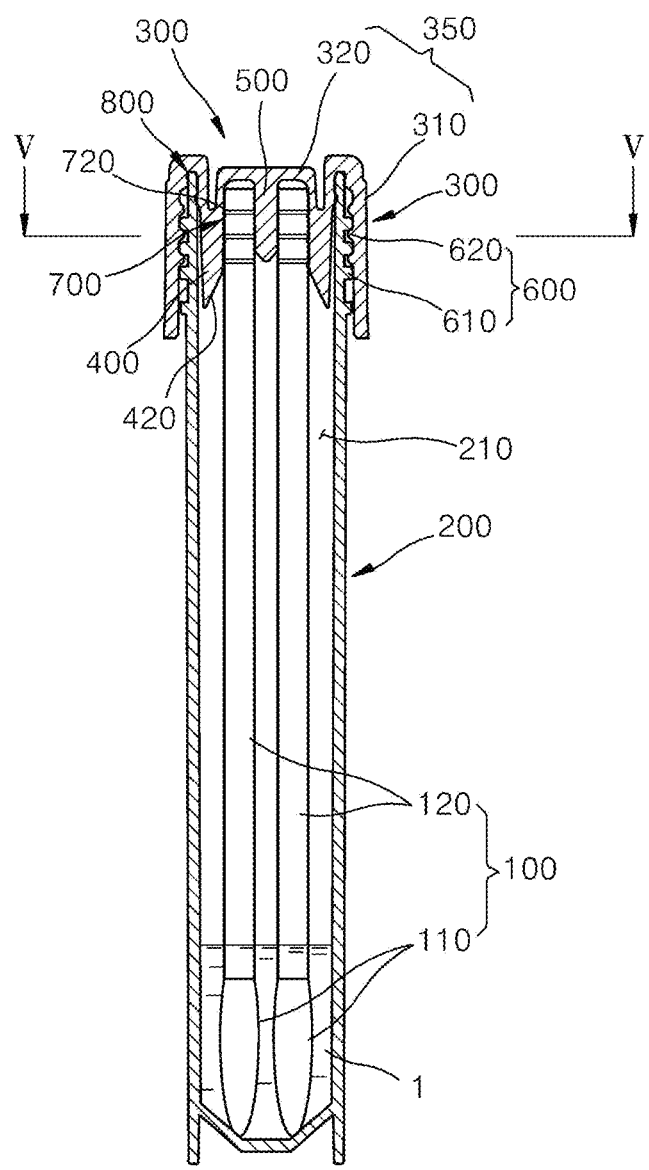
FIG. 3 is a sectional view showing the internal structure in the state in which the container cover for specimen storage according to the embodiment of the present invention is coupled to the container.

Referring to FIG. 3, the specimen preservation container 200 may be configured such that the shielded one-side bottom surface of the specimen preservation container is formed in a concave shape, as shown.

The specimen preservation container 200 may be made of a transparent material to allow the inspector to view the interior or an opaque material.

The specimen preservation container 200 may be made of, but is not limited to, a synthetic resin-based material that is easy to manufacture and economical.

Hereinafter, a container cover 300 for specimen storage according to an embodiment of the present invention will be described.

The container cover 300 for specimen storage according to the embodiment of the present invention may be detachably screwed to the open insertion hole 230 side of the specimen preservation container 200 to open and close the receiving space 210 such that the specimen collection swab 100 can be stored and transported.

Furthermore, the container cover 300 for specimen storage according to the embodiment of the present invention may be coupled to the one or more specimen collection swabs 100 when coupled to the specimen preservation container 200 such that, when separated from the specimen preservation container 200, the specimen collection swabs 100 are also removed from the specimen preservation container 200.

Figure 4:
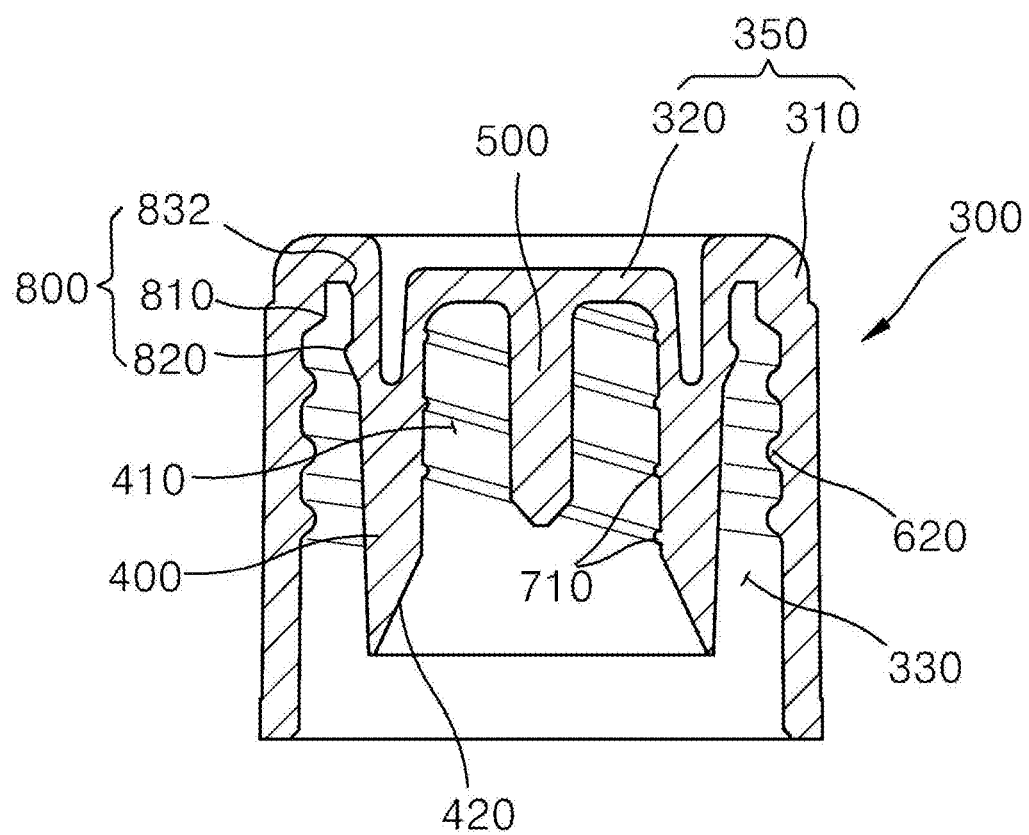
FIG. 4 is a sectional view showing a detailed configuration of the container cover for specimen storage according to the embodiment of the present invention.

Referring to FIG. 4, the container cover 300 for specimen storage includes a cover body 350, an insertion coupling portion 400, a protruding fitting portion 500, a separation prevention portion 700, and an airtight portion 800.

The cover body 350 includes a tubular side portion 310 coupled to an outer circumferential surface of one side of the specimen preservation container 200 and a bottom portion 320 coupled to one end of the side portion 310 to shield the insertion hole 230.

Here, the insertion coupling portion 400 and the protruding fitting portion 500 may be coupled to the bottom portion 320 toward a lower surface facing the specimen preservation container 200, i.e., the receiving space 210.

In the container cover 300 for specimen storage, an interstitial space 330 is defined between an inner circumferential surface of the side portion 310 and an outer circumferential surface of the insertion coupling portion 400, and one end of the specimen preservation container 200 may be inserted into and coupled to the interstitial space 330.

The interstitial space 330 may be formed such that the width of the interstitial space is gradually reduced from an inlet, through which the specimen preservation container 200 is inserted, to the bottom portion 320, whereby easy insertion of the specimen preservation container 200 may be achieved, and the insertion end of the specimen preservation container 200 and the container cover 300 for specimen storage may come into tighter contact with each other.

The container cover 300 for specimen storage may be detachably coupled to the specimen preservation container 200 via a detachment means 600. A screw coupling structure capable of securing fastening force and airtightness may be applied the detachment means 600, as shown.

The detachment means 600 includes a first screw thread 610 formed on an outer circumferential surface of an upper end of the specimen preservation container 200 and a second screw thread 620 formed on an inner surface of the side portion 310 of the container cover 300 for specimen storage so as to be engaged with the first screw thread 610.

Here, although a screw coupling structure is applied to the detachment means 600 in a preferred embodiment, various other detachment structures, such as a snap structure, may be used as long as it is possible to secure fastening force and airtightness.

The insertion coupling portion 400 is formed so as to protrude from the bottom portion 320 of the cover body 350 toward the receiving space 210, an inner space 410 is formed in the insertion coupling portion, and the stick portions 120 of the one or more specimen collection swabs 100 may be inserted and fitted into the inner space 410.

The insertion coupling portion 400 may be formed so as to have an inclined surface 420 formed at an exposed end and inclined downward from the outer surface to the inner surface thereof. The inclined surface 420 serves to guide the stick portion 120 such that stick portion can be more easily inserted into the inner space 410 without being caught by the end.

Figure 5:
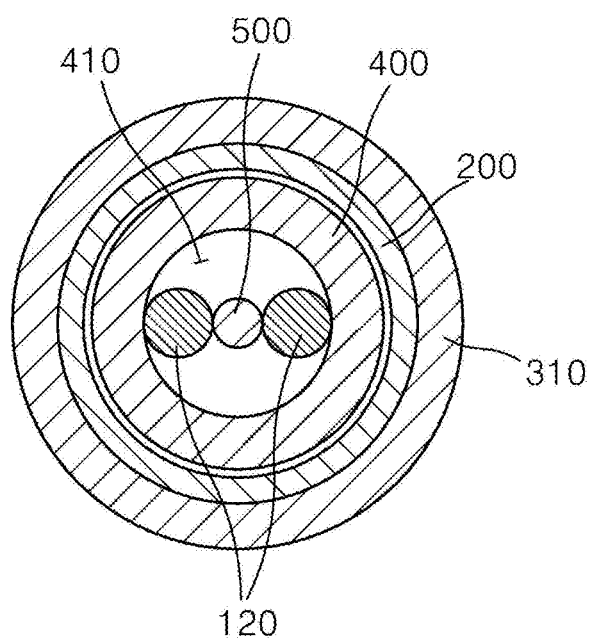
FIG. 5 is a sectional view taken along line V-V of FIG. 3.

Referring to FIG. 5, the insertion coupling portion 400 may have the shape of a cylindrical tube and may be formed in the shape of a closed loop in plan section, whereby the ends of the stick portions 120 may be fitted into and received at an arbitrary position in a cylindrical inner space 410.

Specifically, when the container cover 300 for specimen storage is coupled to the specimen preservation container 200 in the state in which a plurality of specimen collection swabs 100 is disposed in the specimen preservation container 200 by insertion, the stick portion 120 may be fitted into and coupled to an arbitrary position in the inner space 410 of the insertion coupling portion 400 without the need to separately set the coupling position of the stick portion 120.

The planar insertion area of the internal space 410 of the insertion coupling portion 400 may be variously set by considering the diameter and maximum number of the stick portions 120 to be inserted into the internal space 410.

The protruding fitting portion 500 may be located in the center of the inner space 410, and may be formed so as to protrude from a lower surface of the container cover 300 for specimen storage, i.e., the bottom portion 320, toward the receiving space 210.

The one or more stick portions 120 may be fitted into and coupled to an arbitrary position between the outer surface of the protruding fitting portion 500 and the inner surface of the insertion coupling portion 400, and the number of the stick portions 120 that can be fitted thereinto and coupled thereto may optionally be set to one to a plurality.

Diameters and positions may be set such that the distance between the outer circumferential surface of the protruding fitting portion 500 and the inner circumferential surface of the insertion coupling portion 400 corresponds to the diameter of the stick portion 120, whereby the stick portion 120 is fitted between the outer circumferential surface of the protruding fitting portion 500 and the inner circumferential surface of the insertion coupling portion 400.

On the assumption that the stick portions 120 have the same diameter, the protruding fitting portion 500 may be located on the center axis of the inner space 410, i.e., in the center of the inner space 410 in plan, as shown.

The protruding fitting portion 500 may be formed in a cylindrical shape, as shown; however, the present invention is not limited thereto.

As described above, the protruding fitting portion 500 is located in the inner space 410 such that the stick portion 120 having the set diameter can be fitted between the insertion coupling portions 400.

In addition, coupling of the stick portions 120 is achieved by the protruding fitting portion 500 in the state in which the number of the stick portions 120 that can be fitted into and coupled to an arbitrary position in the inner space 410 is optionally set to one to a plurality.

Figure 6:
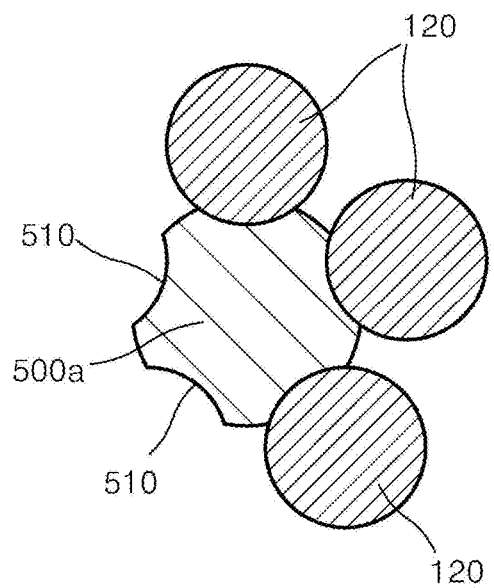
FIG. 6 is a plan sectional view showing another embodiment of the container cover for specimen storage according to the embodiment of the present invention in which a contact recess is formed in a protruding fitting portion.

FIG. 6 is a view showing another embodiment of the protruding fitting portion 500a. Referring to FIG. 6, the protruding fitting portion 500a may be provided at an outer circumferential surface thereof with a contact recess 510 formed in a longitudinal direction.

The contact recess 510 may be formed in an arc sectional shape so as to correspond to the shape of a part of the outer circumferential surface of the stick portion 120 such that part of the outer circumferential surface of the stick portion 120 is seated in the contact recess in a contact state, and may guide the stick portions 120 so as to be located at the set positions.

The depth of the contact recess 510 may be set in consideration of the positioning function, etc. of the stick portion 120, and the number of contact recesses may be variously set.

Although not shown, the protruding fitting portion 500 may be provided with a spiral protrusion formed as the result of being spirally wound a plurality of times along the outer circumferential surface thereof. Similarly to the catching portion 710, when the cover body 350 is rotated in a state of being screwed to the specimen preservation container 200, the protrusion 720 of the stick portion 120 may be guided along the spiral protrusion, and the spiral protrusion may be caught by the protrusion 720 of the stick portion 120 in a contact state, whereby it is possible to prevent separation of the stick portion 120.

Although not shown, the protruding fitting portion 500 may have a convex catching protrusion formed along an outer circumferential surface of an exposed end thereof, whereby it is possible to prevent separation of the inserted stick portion 120.

The separation prevention portion 700 serves to prevent the specimen collection swab 100 from being separated from the cover body 350.

Figure 7:
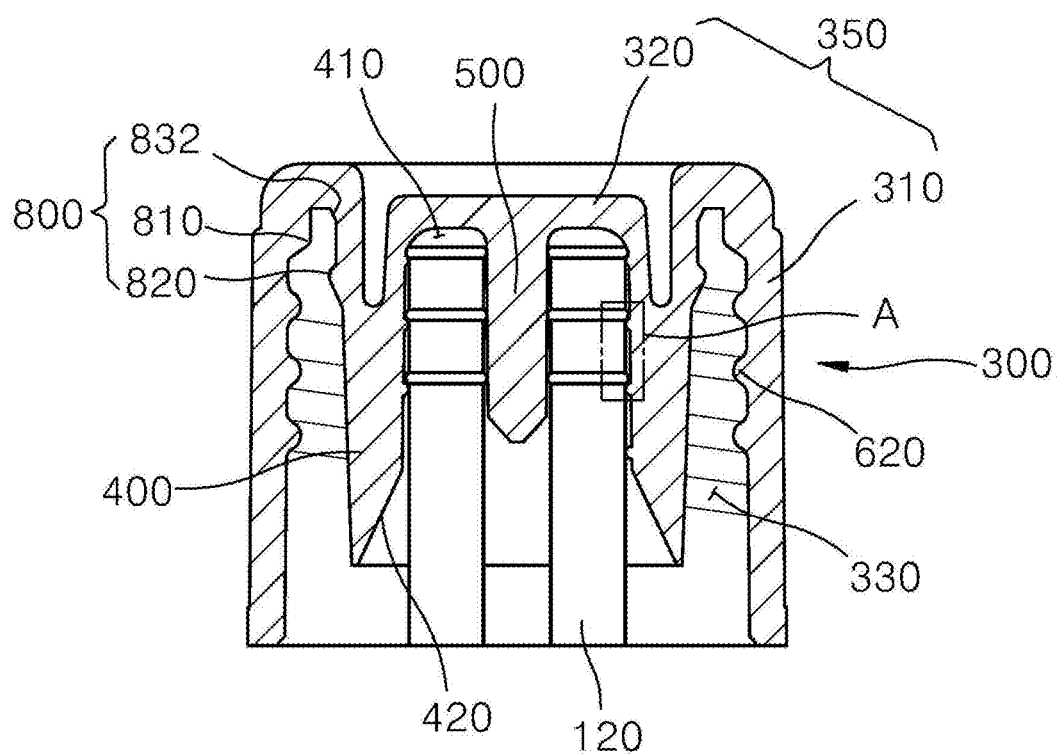
FIG. 7 is a sectional view showing a coupling structure between the container cover for specimen storage according to the embodiment of the present invention and a specimen collection swab.
Figure 8:
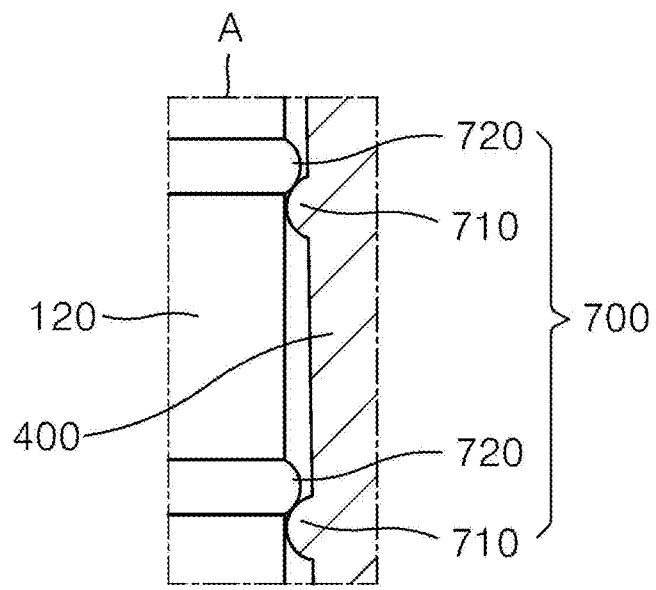
FIG. 8 is an enlarged view of part "A" of FIG. 7.

Referring to FIGS. 7 and 8, the separation prevention portion 700 is provided at the insertion coupling portion 400 so as to be caught by the stick portions 120 in a contact state when the cover body 350 is coupled to the specimen preservation container 200 to prevent the stick portions 120 from being separated from the insertion coupling portion 400.

When the cover body 350 is coupled to the specimen preservation container 200, the separation prevention portion 700 is caught by the stick portion 120 in a contact state, whereby, when the container cover 300 for specimen storage is separated from the specimen preservation container 200, separation of the stick portions 120 from the insertion coupling portion 400 may be prevented.

The separation prevention portion 700 includes a catching portion 710 formed at an inner surface of the insertion coupling portion 400 so as to protrude therefrom and formed along the inner surface thereof.

When the stick portion 120 is fitted into the insertion coupling portion 400, the catching portion 710 is caught by a protrusion 720 of the stick portion 120, which will be described later, whereby separation of the stick portion 120 from the insertion coupling portion 400 may be prevented.

As shown, the catching portion 710 may be formed in the form of a recess, into which the protrusion 720 is inserted so as to be caught thereby, instead of protruding from the insertion coupling portion 400, and may also be formed in various shapes, such as forming the protrusion 720 in the shape of a recess and forming the catching portion 710 in the shape of a protrusion, as long as the above purpose can be achieved.

When the cover body 350 is screwed to the specimen preservation container 200, the stick portion 120 may be guided toward the lower surface of the cover body 350 along the catching portion 710 of the separation prevention portion 700 so as to be fitted into and coupled to the insertion coupling portion.

To this end, the catching portion 710 may be formed so as to be spirally wound a plurality of times around the inner circumferential surface of the insertion coupling portion 400.

This is based on consideration of the rotation of the cover body 350 and the insertion coupling portion 400 when the container cover 300 for specimen storage and the specimen preservation container 200 are screwed to each other, wherein the catching portion 710 is spirally formed in response to the rotation of the cover body 350 by screw coupling, whereby, when the insertion coupling portion 400 is rotated, the protrusion 720 is guided along the catching portion 710 toward the bottom portion 320 so as to be fitted into and coupled to the insertion coupling portion.

Meanwhile, the stick portion 120 may include a protrusion 720 formed on an outer surface of the other end thereof so as to be caught by the catching portion 710 in a contact state.

Here, the protrusion 720 may be formed along an outer circumferential surface of the stick portion 120 so as to annularly protrude therefrom, and a plurality of protrusions may be spaced apart from each other in a longitudinal direction of the stick portion 120.

The protrusion 720 may be formed in a hemispherically convex shape in a direction in which the stick portion 120 is inserted, as shown. However, this is merely an embodiment, and the protrusion may be formed in various shapes.

Although not shown, the separation prevention portion 700 may further include a separation prevention protrusion formed as the result of being spirally wound a plurality of times along an outer circumferential surface of the protruding fitting portion 500. Similarly to the catching portion 710, when the container cover 300 for specimen storage is rotated, the separation prevention protrusion may be caught by the protrusion 720 in a contact state while guiding the protrusion, whereby it is possible to prevent separation of the stick portion 120.

Figure 9:
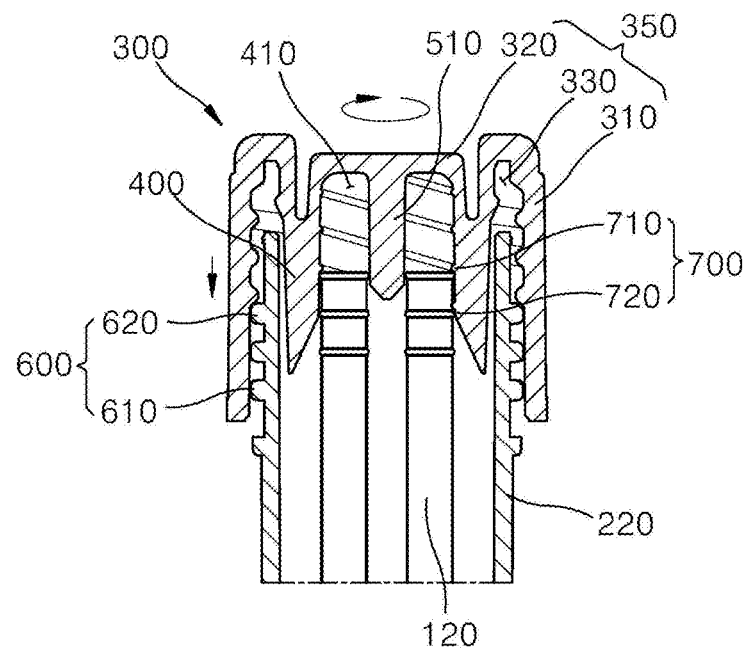
FIGS. 9 to 11 are sectional views showing insertion of the specimen collection swab and the operation of a separation prevention portion in response to rotation of the container cover for specimen storage according to the embodiment of the present invention of FIG. 6.
Figure 10:
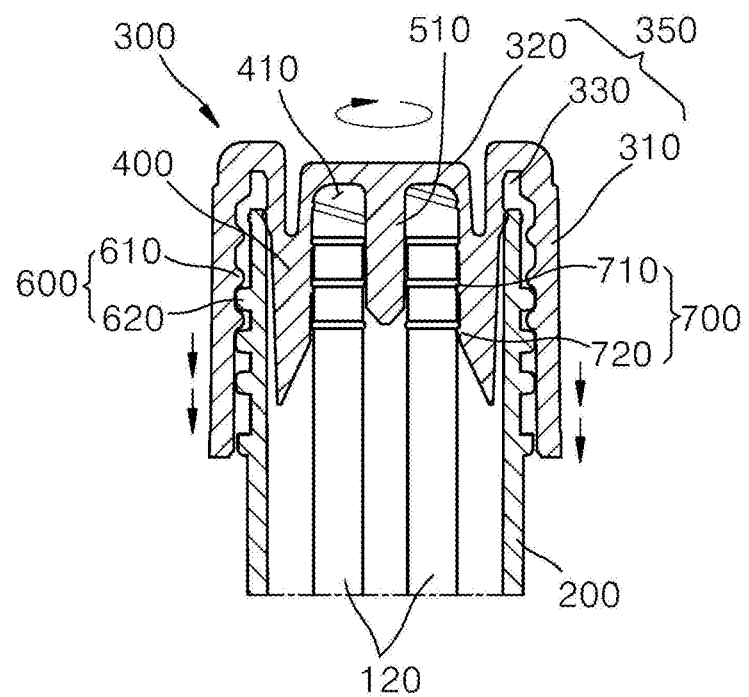
Figure 11:
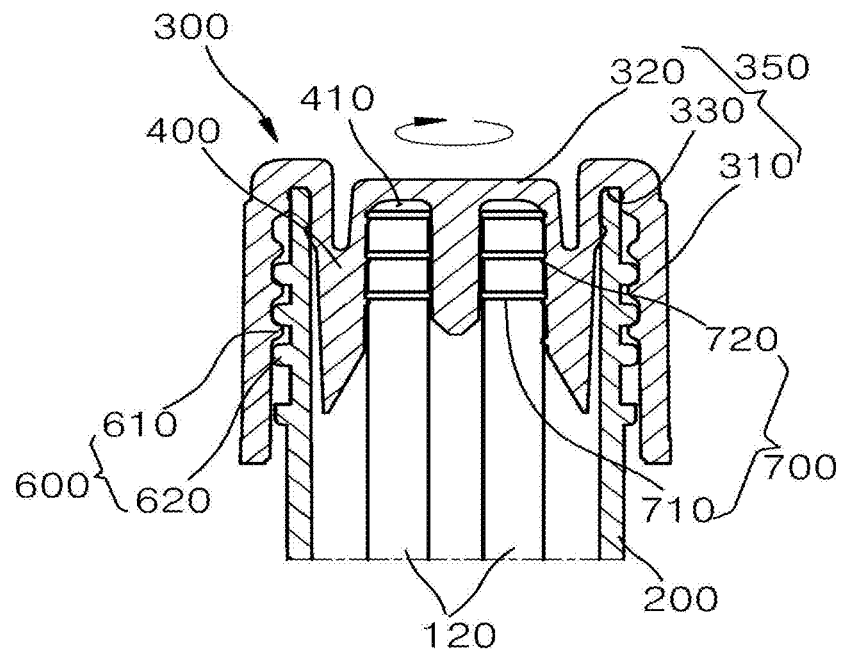

FIGS. 9 to 11 are views showing fitting and coupling of the specimen collection swab 100 by rotation of the container cover 300 for specimen storage.

Referring first to FIG. 9, when the container cover 300 for specimen storage is coupled to the specimen preservation container 200 so as to shield the insertion hole 230. At this time, upper ends of the stick portions 120 of the plurality of specimen collection swabs 100 inserted into the specimen preservation container 200 are fitted between the insertion coupling portion 400 and the protruding fitting portion 500.

FIG. 10 shows that the inspector rotates the container cover 300 for specimen storage to couple the container cover 300 for specimen storage to the specimen preservation container 200 by screw coupling in the state of FIG. 9.

At this time, as the container cover 300 for specimen storage is rotated in a state of being fastened to the specimen preservation container 200 by screw coupling, the container cover for specimen storage moves downward toward the specimen preservation container 200.

As a result, the stick portion 120 is inserted more deeply in the inner space 410 toward the bottom portion 320. Here, the protrusion 720 is guided toward the bottom portion 320 along the spiral catching portion 710 by rotation of the insertion coupling portion 400.

FIG. 11 shows the state in which the container cover 300 for specimen storage of FIG. 10 is further rotated. Referring to the figure, the container cover 300 for specimen storage is further rotated such that the open end of the specimen preservation container 200 is located adjacent to the bottom portion 320 of the cover body 350, whereby the container cover for specimen storage is airtightly coupled to the specimen preservation container 200 in tight contact therewith.

The stick portion 120 is further inserted toward the bottom portion 320 in the insertion coupling portion 400, and the protrusions 720 of the stick portion 120 are caught by the catching portion 710, whereby separation of the stick portion 120 from the insertion coupling portion 400 is prevented.

The catching portion 710 is spirally formed on the inner circumferential surface of the insertion coupling portion 400, as described above. When the container cover 300 for specimen storage is rotated by screw coupling, therefore, the catching portion may guide the protrusions 720, whereby easier catching contact may be achieved.

When the inspector separates the container cover 300 for specimen storage from the specimen preservation container 200 for inspection in this state, the specimen collection swab 100 is removed in a state of being coupled to the insertion coupling portion 400, and therefore it is not necessary for the inspector to separately remove the specimen collection swab 100 from the specimen preservation container 200.

In a specimen collection and storage kit according to an embodiment of the present invention, it is very important to secure airtightness in a process of storing and transporting a specimen collected from a subject in order to obtain effectiveness of a test by preventing leakage of a specimen and a medium as well as contamination from the outside.

In the present invention, therefore, an airtight portion 800 may be formed at each of the container cover 300 for specimen storage and the specimen preservation container 200, which are coupled to each other, in order to further improve airtightness.

When the specimen preservation container 200 is fitted into and coupled to the interstitial space 330 between the inner circumferential surface of the cover body 350 and the outer surface of the insertion coupling portion 400, the airtight portion 800 may be formed at each of the inner circumferential surface of the side portion 310 and the outer surface of the insertion coupling portion 400, whereby, when the specimen preservation container 200 is fitted into and coupled to the interstitial space 330, the specimen preservation container 200 and the cover body 350 are brought into tight contact with each other, and therefore airtightness may be maintained.

Figure 12:
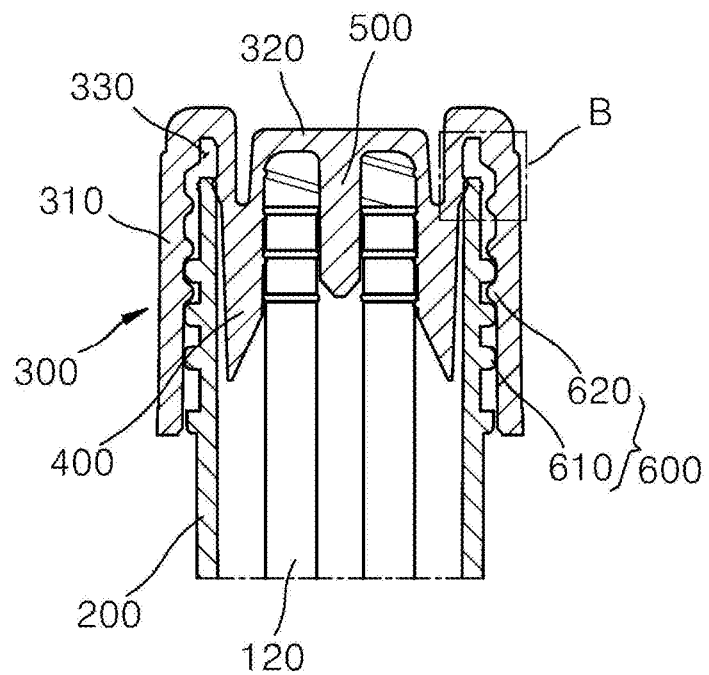
FIG. 12 is a sectional view showing the container cover for specimen storage according to the embodiment of the present invention and a specimen preservation container.
Figure 13:
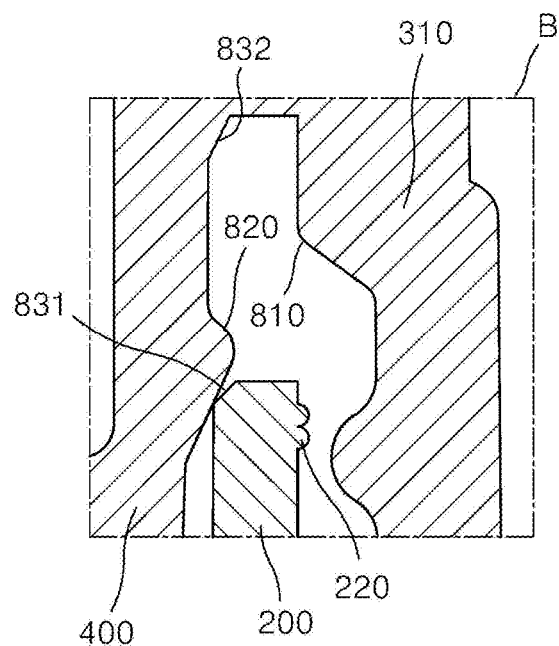
FIG. 13 is an enlarged view of part "B" of FIG. 12.

Referring to FIGS. 12 and 13, the airtight portion 800 may include a first pressing protrusion 810 and a second pressing protrusion 820.

First, the first pressing protrusion 810 may be formed at the inner circumferential surface of the side portion 310 of the cover body 350 so as to protrude therefrom in order to press an outer circumferential surface of one end of the specimen preservation container 200 when the specimen preservation container 200 and the container cover 300 for specimen storage are fastened to each other. Here, the first pressing protrusion 810 may be located adjacent to the bottom portion 320 to press the end of the specimen preservation container 200.

The second pressing protrusion 820 may be formed at the outer circumferential surface of the insertion coupling portion 400 so as to protrude therefrom in order to press an inner circumferential surface of one end of the specimen preservation container 200 when the specimen preservation container 200 and the container cover 300 for specimen storage are fastened to each other. In this case, the second pressing protrusion 820 may be located adjacent to the bottom portion 320 of the container cover 300 for specimen storage to press the end of the specimen preservation container 200.

The first pressing protrusion 810 and the second pressing protrusion 820 may be located so as to be staggered from each other, as shown; however, the positions thereof may be changed. For example, the first pressing protrusion and the second pressing protrusion may be located at the same position on a horizontal line.

Each of the first pressing protrusion 810 and the second pressing protrusion 820 may be formed such that one side thereof is inclined in an insertion direction, as shown, to guide the insertion of the specimen preservation container 200.

According to the foregoing, the airtight portion 800 may press the inside and the outside of one end of the specimen preservation container 200 through the first pressing protrusion 810 and the second pressing protrusion 820, respectively, and block any space that may occur between the specimen preservation container 200 and the container cover 300 for specimen storage, whereby it is possible to improve sealing force and airtightness.

Meanwhile, edges of the specimen preservation container 200 and the container cover 300 for specimen storage have a small area of contact as the edges are in line contact rather than in surface contact, and it is necessary to secure airtightness of the edges as the edges may be separated from each other.

Accordingly, the airtight portion 800 may include a first inclined contact surface 831 and a second inclined contact surface 832 to secure airtightness at the edge of the specimen preservation container 200 in addition to the first pressing protrusion 810 and the second pressing protrusion 820 provided to maintain airtightness at the inner surface and the outer surface of the specimen preservation container 200.

First, the first inclined contact surface 831 may be formed such that an end edge of the specimen preservation container 200 is incised to have an inclined surface.

The second inclined contact surface 832 may be formed at a lower end of the insertion coupling portion 400 that faces the first inclined contact surface 831, and may be formed so as to have an inclination corresponding to the inclination of the first inclined contact surface 831.

When the specimen preservation container 200 is inserted into and coupled to the interstitial space 330, therefore, the first inclined contact surface 831 and the second inclined contact surface 832 come into tight surface contact with each other, whereby airtightness at the edge thereof is secured.

Although the first inclined contact surface 831 and the second inclined contact surface 832 are shown as being formed at the inner circumferential end edge of the specimen preservation container 200, the first inclined contact surface and the second inclined contact surface may be formed at the outer circumferential end edge of the specimen preservation container 200 or at each of the inner and outer circumferential end edges of the specimen preservation container.

Furthermore, the airtight portion 800 may include a protrusion 220 formed on an outer circumferential surface of one end of the specimen preservation container 200 in tight contact with the side portion 310 of the cover body 350. The protrusion 220 may be formed at an outer circumferential surface of an upper end of the specimen preservation container 200 so as to annularly protrude therefrom to press the side portion 310 for tight contact.

A plurality of protrusions 220 may be arranged from the upper end of the specimen preservation container 200 in a longitudinal direction so as to be spaced apart from each other, and the number of the protrusions and the distance between the protrusions may be variously adjusted.

Figure 14:
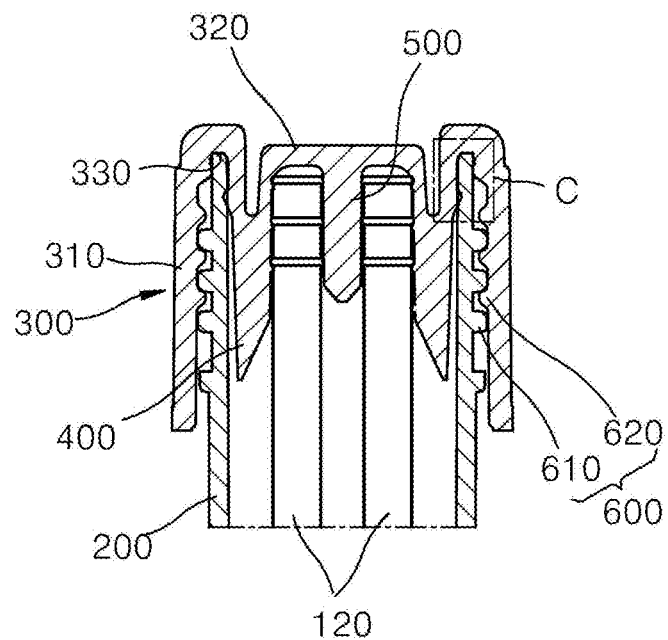
FIG. 14 is a sectional view showing the state in which the container cover for specimen storage according to the embodiment of the present invention is coupled to the specimen preservation container in tight contact therewith as the result of rotation of the container cover in FIG. 12.
Figure 15:
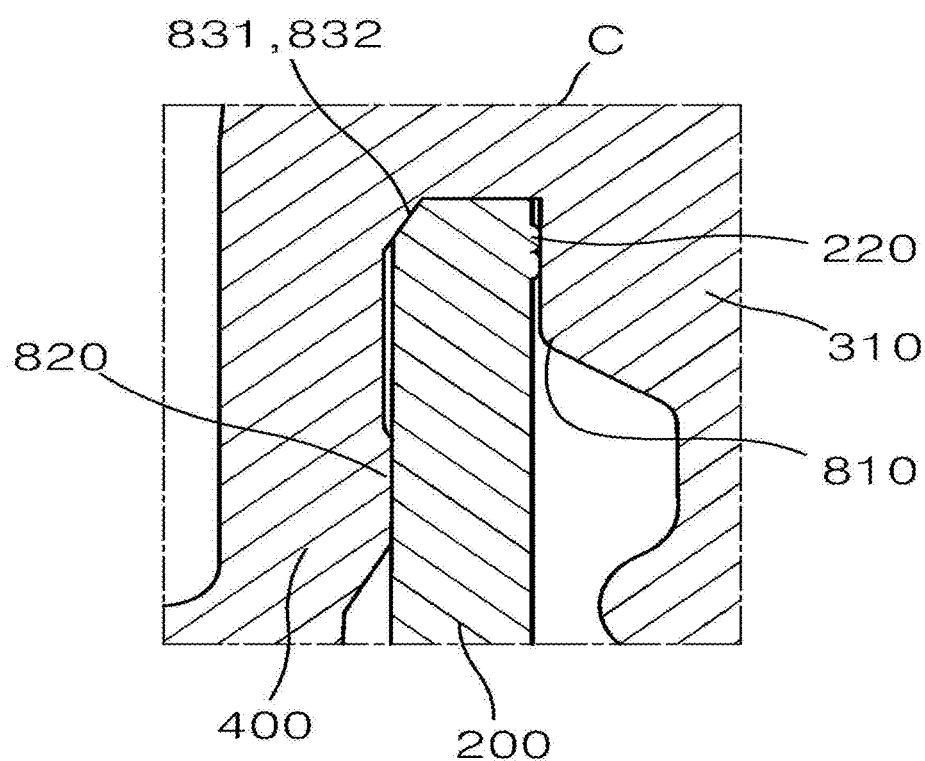
FIG. 15 is an enlarged view of part "C" of FIG. 14.

FIGS. 14 and 15 are views showing the state in which the specimen preservation container 200 and the container cover 300 for specimen storage are fastened to each other and the airtight portion 800.

Referring to the figures, the airtight portion 800 presses the inner circumference surface and the outer circumferential surface of the specimen preservation container 200 through the first pressing protrusion 810 and the second pressing protrusion 820, respectively, such that the ends of the specimen preservation container 200 and the container cover 300 for specimen storage come into tight contact with each other.

In addition, the airtight portion 800 brings the edges of the specimen preservation container 200 and the container cover 300 for specimen storage into tight contact with each other through the first inclined contact surface 831 and the second inclined contact surface 832, whereby overall airtightness may be improved.

The container cover 300 for specimen storage may be made of an elastically deformable material capable of resiliently pressing the specimen storage container 200 fitted into the interstitial space 330, and various materials, including resin-based materials, may be used as the material of the container cover for specimen storage.

Figure 16:
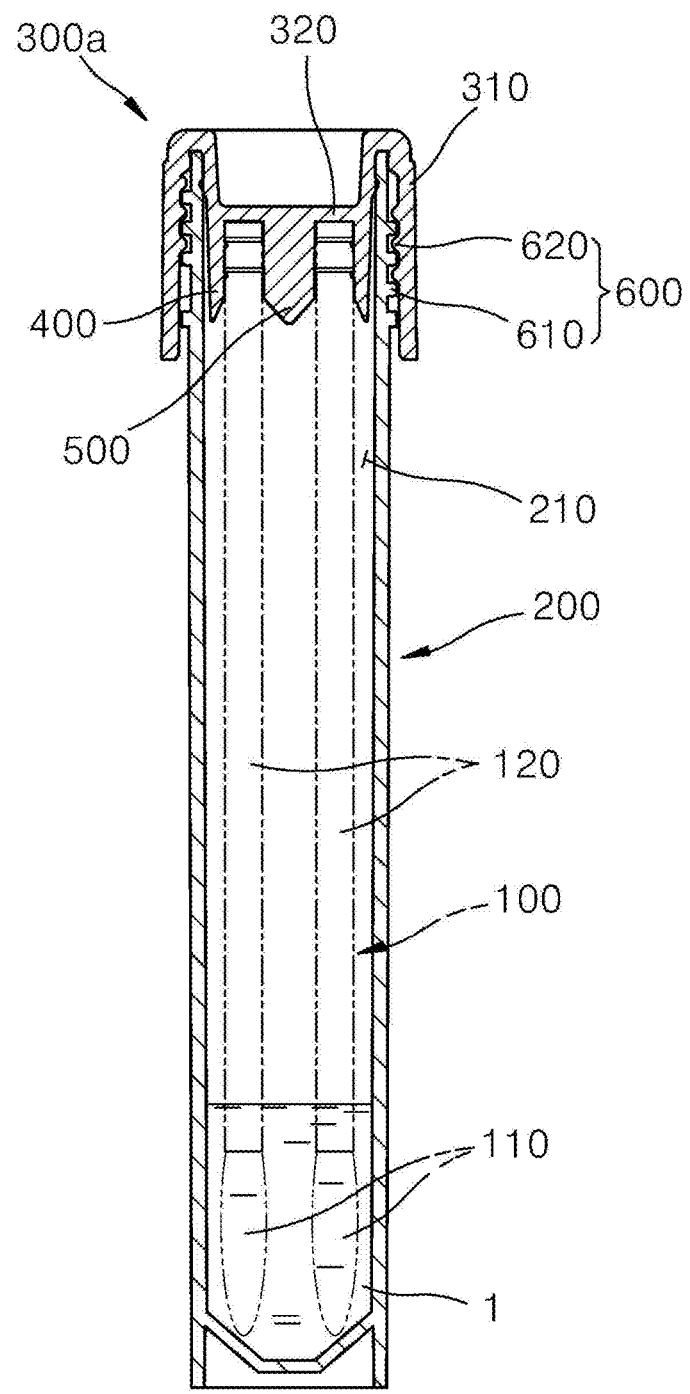
FIG. 16 is a sectional view showing a further embodiment of the container cover for specimen storage according to the embodiment of the present invention.

FIG. 16 is a view showing another embodiment of the container cover for specimen storage 300a. Referring to the figure, the container cover 300a for specimen storage may be configured such that the bottom portion 320 is formed concave toward said receiving space 210 and the protruding fitting portion 500 is formed up to the end of the insertion coupling portion 400. In the specimen collection and storage kit according to the present invention, as described above, the shape of the container cover 300a for specimen storage and the shape, diameter, and length of the protruding fitting portion 500 may be various changed as long as the purpose of each of the above components can be achieved.

Figure 17:
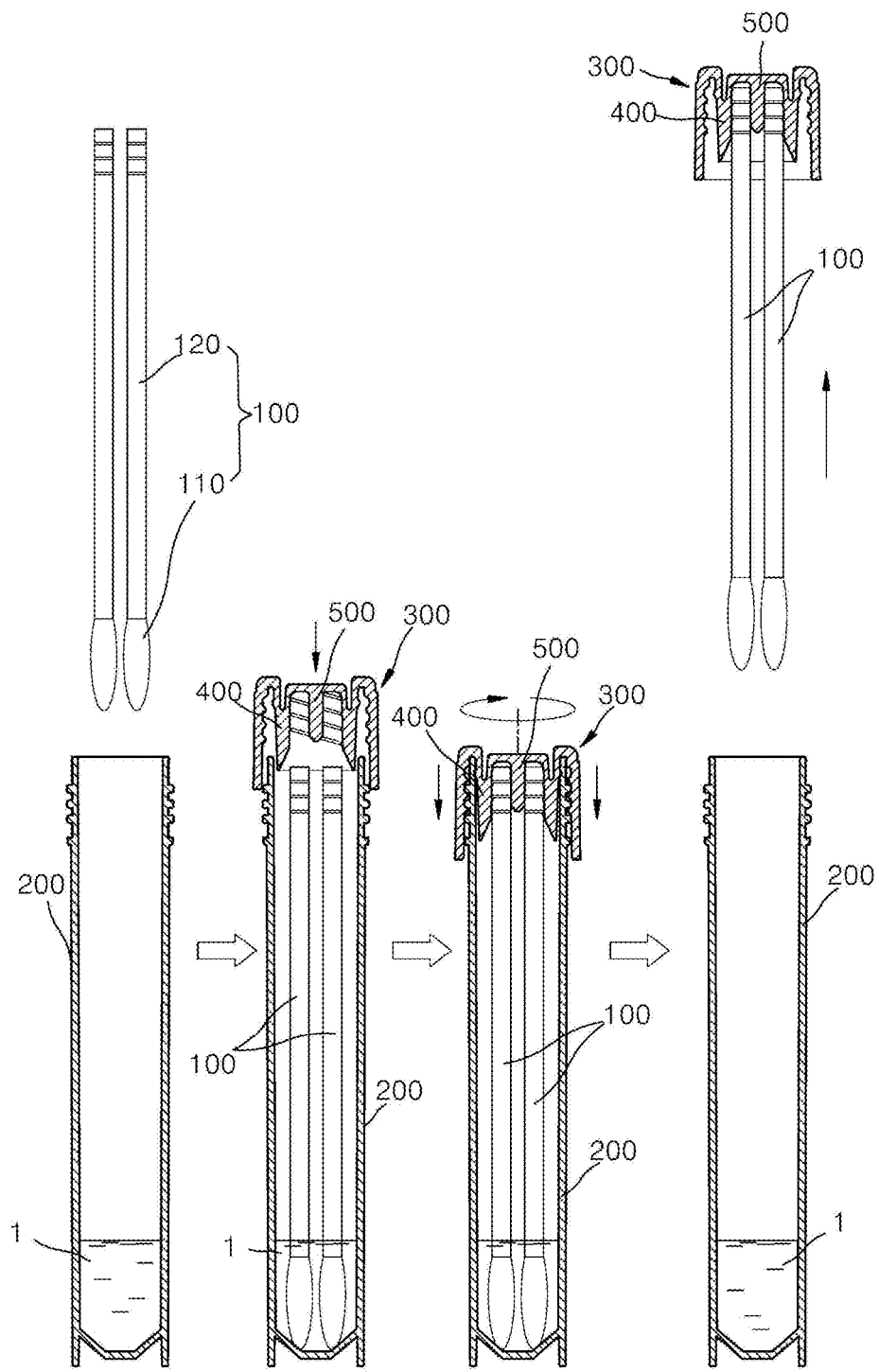
FIG. 17 is a view showing a process of using the container cover for specimen storage according to the embodiment of the present invention.

FIG. 17 is a view showing a use example of the container cover 300 for specimen storage according to the embodiment of the present invention. Referring to the figure, the inspector first collects a specimen from a subject through the specimen collection swab 100 and inserts the specimen collection swab into the receiving space 210 of the specimen preservation container 200.

Subsequently, the inspector couples the container cover 300 for specimen storage to the open one side of the specimen preservation container 200 to shield the specimen preservation container 200. At this time, the stick portion 120 of the specimen collection swab 100 is fitted into the insertion coupling portion 400.

At this time, the inspector rotates the container cover 300 for specimen storage so as to be screwed to the specimen storage container 200. In this process, the stick portion 120 is further inserted inwardly of the insertion coupling portion 400. At this time, the protrusions 720 are guided inwardly of the insertion coupling portion 400 along the catching portion 710 and are caught by the catching portion 710 in a contact state, as described above.

Subsequently, when the inspector separates the container cover 300 for specimen storage, the specimen collection swab 100 comes out in a state of being fitted in the container cover 300 for specimen storage by the separation prevention portion 700, as shown.

The invention has been described with reference to the embodiment shown in the drawings, but this is illustrative only, and a person having ordinary skill in the art to which the present invention pertains will understand that various modifications and other equivalent embodiments are possible therefrom. The true scope of technical protection of the present invention will therefore be determined by the technical ideas of the appended claims.

INDUSTRIAL APPLICABILITY

The present invention is applicable to a specimen collection instrument.

The invention claimed is:

1. A container cover for specimen storage, the container cover comprising:
   a cover body comprising a tubular side portion and a bottom portion coupled to one end of the tubular side portion, the cover body being detachably screwed to open one side of a specimen preservation container in which one or more specimen collection swabs are provided by insertion, each of the one or more specimen collection swabs including a stick portion;

an insertion coupling portion formed so as to protrude from the bottom portion toward the specimen preservation container, the insertion coupling portion having an inner space defined therein such that the stick portion can be inserted and fitted into and coupled to the inner space; and a protruding fitting portion located in the inner space, the protruding fitting portion being formed so as to protrude from the bottom portion, the protruding fitting portion being configured such that the stick portion is fitted and coupled between an outer surface of the protruding fitting portion and an inner surface of the insertion coupling portion, wherein when the specimen preservation container is coupled to the container cover, the stick portion is fitted into and coupled to a position in the inner space, the container cover further comprising a separation prevention portion provided at the insertion coupling portion, the separation prevention portion being caught by the stick portion in a contact state when the cover body is coupled to the specimen preservation container to prevent the stick portion from being separated from the insertion coupling portion, wherein the separation prevention portion comprises a catching portion formed at the inner surface of the insertion coupling portion so as to protrude therefrom and formed along the inner surface, when the cover body is screwed to the specimen preservation container, the stick portion is guided toward a lower surface of the cover body along the catching portion so as to be fitted into and coupled to the insertion coupling portion, the catching portion is formed so as to be spirally wound a plurality of times around the inner surface of the insertion coupling portion in response to rotation of the container cover by screw coupling, and when the cover body is screwed to the specimen preservation container, the stick portion is guided toward the lower surface of the cover body along the spiral catching portion so as to be fitted into and coupled to the insertion coupling portion.

2. The container cover according to claim 1, wherein
the insertion coupling portion is formed in a shape of a cylindrical tube, and
the stick portion is inserted into a position in the cylindrical inner space.

3. The container cover according to claim 1, wherein the insertion coupling portion is configured such that an exposed end thereof is formed so as to be inclined downward toward an inside thereof to guide the stick portion.

4. The container cover according to claim 1, wherein the protruding fitting portion is formed in a cylindrical shape.

5. The container cover according to claim 1, wherein
the specimen preservation container is fitted into and coupled to an interstitial space between an inner circumferential surface of the cover body and an outer surface of the insertion coupling portion, and
the container cover further comprises an airtight portion formed at each of an inner circumferential surface of the tubular side portion and the outer surface of the insertion coupling portion, the airtight portion being configured to allow the specimen preservation container and the cover body to come into tight contact with each other such that airtightness is maintained when the specimen preservation container is fitted into and coupled to the interstitial space.

6. The container cover according to claim 5, wherein the airtight portion comprises:
a first pressing protrusion formed at the inner circumferential surface of the tubular side portion of the cover body so as to protrude therefrom, the first pressing protrusion being configured to press an outer circumferential surface of the specimen preservation container; and
a second pressing protrusion formed at an outer circumferential surface of the insertion coupling portion so as to protrude therefrom, the second pressing protrusion being configured to press an inner circumferential surface of the specimen preservation container.

* * * * *